United States Patent
Lin et al.

(10) Patent No.: US 8,686,178 B2
(45) Date of Patent: *Apr. 1, 2014

(54) DERIVATIVE OF 18β-GLYCYRRHETINIC ACID APT TO SUPPRESS CANCER CELLS

(75) Inventors: Chun-Nan Lin, Kaohsiung (TW); Kai-Wei Lin, Kaohsiung (TW); A-Mei Huang, Kaohsiung (TW); Tzyh-Chyuan Hour, Kaohsiung (TW); Shyh-Chyun Yang, Kauhsiung (TW); Yeong-Shiau Pu, Kaohsiung (TW); Jan-Gowth Chang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 92 days.

This patent is subject to a terminal disclaimer.

(21) Appl. No.: 13/420,177

(22) Filed: Mar. 14, 2012

(65) Prior Publication Data

US 2013/0109752 A1    May 2, 2013

(30) Foreign Application Priority Data

Oct. 27, 2011  (TW) ............................... 100139104 A

(51) Int. Cl.
*C07C 69/75* (2006.01)
*C07C 233/58* (2006.01)
*A61K 31/122* (2006.01)

(52) U.S. Cl.
USPC .................................. 560/6; 560/7; 564/152

(58) Field of Classification Search
None
See application file for complete search history.

(56) References Cited

U.S. PATENT DOCUMENTS

| 7,790,759 | B2 | 9/2010 | Wang et al. |
| 8,329,940 | B2 * | 12/2012 | Lin et al. ....................... 562/498 |
| 2009/0076032 | A1 | 3/2009 | Ward et al. |
| 2011/0039922 | A1 | 2/2011 | Lin et al. |

OTHER PUBLICATIONS

Lin, Kai-Wei et al., "18β-Glycyrrhetinic acid derivatives induced mitochondrial-mediated apoptosis through reactive oxygen species-mediated p53 activation in NTUB1 cells", Bioorganic & Medicinal Chemistry 19, May 30, 2011 pp. 4274-4285.

Maitraie, et al.,Synthesis, anti-inflammatory, and antioxidant activities of 18β- . . . oxidase inhibitors, Bioorganic & Medicinal Chemistry, Feb. 21, 2009, pp. 2785-2792, vol. 17.

Csuk et al., Synthesis and antitumor activity of ring A modified glycyrrhetinic acid derivatives, European Journal of Medicinal Chemistry, Aug. 31, 2011, pp. 5356-5369, vol. 46.

* cited by examiner

*Primary Examiner* — Brian J Davis
(74) *Attorney, Agent, or Firm* — Muncy, Geissler, Olds & Lowe, P.C.

(57) ABSTRACT

The present invention is correlated with a derivative of 18β-glycyrrhetinic acid apt to suppressing cancer cells, which is selected from a group comprising of structure I and structure II:

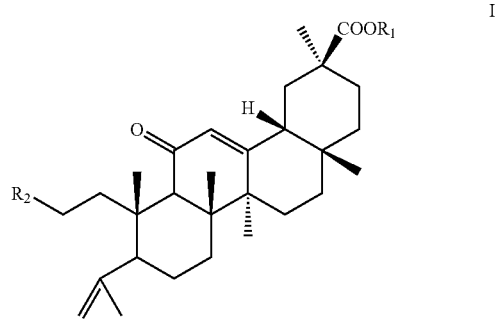

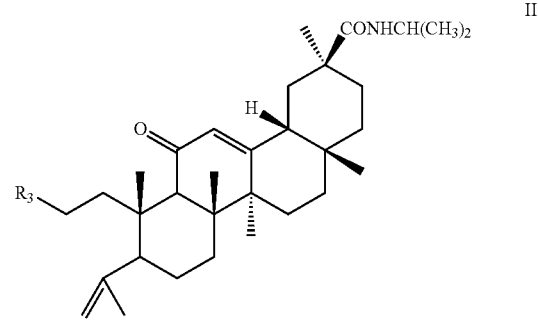

wherein residue $R_1$ is selected from one of $CH_3$ and $CH_2C_6H_5$, residue $R_2$ is selected from one of $COOCH_3$, $COOCH_2CH_3$, $COOCH(CH_3)_2$, $CONHCH_2CH_3$, $CONHCH_2CH_2CH_3$, and $CONHCH_2(CH_3)_2$, and residue $R_3$ is selected from one of $COOCH_2CH_3$, $COOCH(CH_3)_2$, $CONHCH_2CH_3$, $CONHCH_2CH_2CH_3$, and $CONHCH_2(CH_3)_2$.

2 Claims, 9 Drawing Sheets

DERIVATIVE OF 18β-GLYCYRRHETINIC ACID APT TO SUPPRESS CANCER CELLS

BACKGROUND OF THE INVENION

1. Field of the Invention

The present invention relates to a chemical compound apt to suppress cancer cells and a method for synthesizing the said chemical compound, particularly to derivatives of 18β-glycyrrhetinic acid apt to suppress cancer cells and a method for synthesizing the derivatives of 18β-glycyrrhetinic acid.

2. Description of the Related Art

Cancer mainly refers to unregulated and uncontrollably cell proliferation and migration caused by genetic mutation, leading to various incidences of abnormality hyperplasia of cell invading nearby tissues or organs, metastasis through lymphatic system or vessel system, and malignant neoplasm.

Generally, cancer pathogenesis is related to mutation occurred on two types of genes: oncogenes, that drive growth and reproduction of cells, and tumor suppressor genes, which inhibit cell division, development and existence. Accordingly, it is supposed to suppress cancer cells by administrating expression of tumor suppressor genes, such as p53, to an affective part, activating p53 protein when DNA has sustained damage, holding the cell cycle at the G1/G2 stage for repairing damage, and finally initiating apoptosis if the DNA damage is irreparable.

In conventional arts, some anti-cancer drugs, for example cisplatin (cis-diamminedichloroplatinum II, CDDP), are widely used in a treatment for suppressing tumor, including ovarian cancer, germinoma, oesophageal cancer, lung cancer, bladder cancer, cervical cancer, or endometrial carcinoma. However, with the treatment of such anti-cancer drugs, patients usually suffer from intolerable side effects, including vomiting, anemia, hair loss, and immune system disorders, such as decrease in lymphocytes and platelets, and finally even leads to serious drug-resistance.

Hence there is a pressing need of providing a chemical compound, being highly efficient in tumor suppression and sharing synergistic effects with conventional anti-cancer drugs, in order to improve the disadvantages of conventional drugs and develop a new medication for suppressing cancer cells.

SUMMARY OF THE INVENTION

The primary objective of this invention is to provide a derivative of 18β-glycyrrhetinic acid, which can induce the generation of reactive oxygen species (ROS), and activate the tumor suppressor gene p53 in cancer cells, apt to decrease the mitochondrial membrane potential (MMP) and to lead to apoptosis of cancer cells.

The secondary objective of this invention is to provide a synthesized method of the said derivatives of 18β-glycyrrhetinic acid so as to industrialize the production of the said derivative of 18β-glycyrrhetinic acid via a chemical synthesis method.

Another objective of this invention is to provide a medication for suppressing cancer cells, comprising at least one of the said derivatives of 18β-glycyrrhetinic acid and a medicine acceptable carrier, which can suppress cancer cells efficiently.

A derivative of 18β-glycyrrhetinic acid apt to suppress cancer cell, being selected from a group, comprises structure I and structure II:

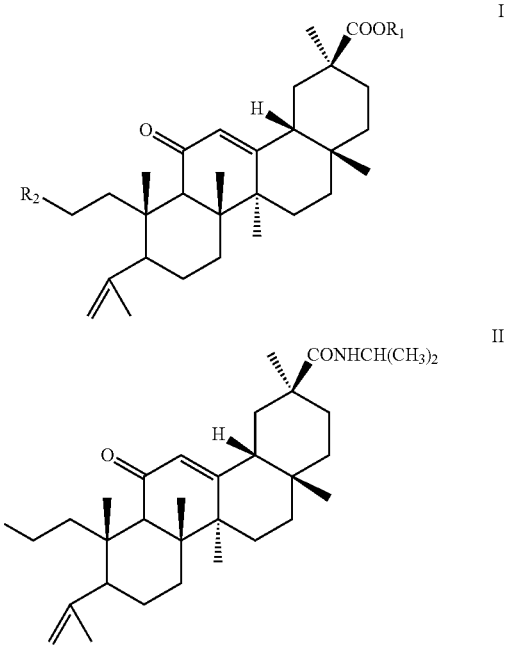

wherein residue R1 is selected from one of $CH_3$ and $CH_2C_6H_5$, residue $R_2$ is selected from one of $COOCH_3$, $COOCH_2CH_3$, $COOCH(CH_3)_2$, $CONHCH_2CH_3$, $CONHCH_2CH_2CH_3$ and $CONHCH_2(CH_3)_2$, and residue $R_3$ is selected from one of $COOCH_2CH_3$, $COOCH(CH_3)_2$, $CONHCH_2CH_3$, $CONHCH_2CH_2CH_3$ and $CONHCH_2(CH_3)_2$.

A medication for suppressing cancer cell comprises a least one of the said derivative of 18β-glycyrrhetinic acid and a medicine acceptable carrier.

A method for synthesizing derivatives of 18β-glycyrrhetinic acid comprises steps of preparing and oxidizing a derivative of 18β-glycyrrhetinic acid to obtain a first compound; and conducting an esterification of the first compound and obtaining a second compound, wherein the residue C-30 of the second compound is an alkyl group or an aromatic group.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention relates to a derivative of 18β-glycyrrhetinic acid apt to suppress cancer cell which is selected from a group comprising of structure I and structure II:

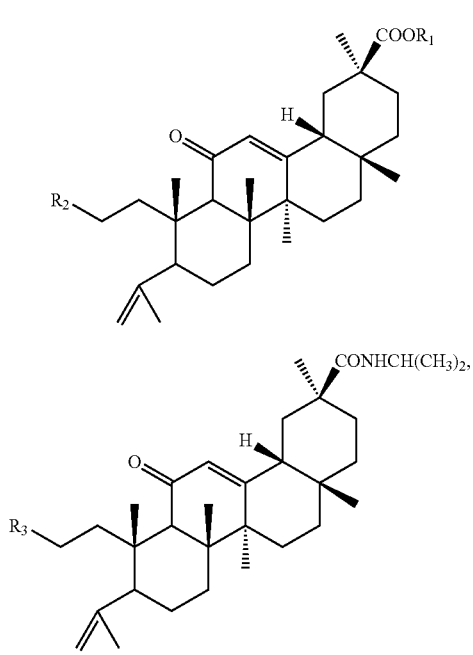

with a residue $R_1$ being selected from one of $CH_3$ and $CH_2C_6H_5$, a residue $R_2$ being selected from one of $COOCH_3$, $COOCH_2CH_3$, $COOCH(CH_3)_2$, $CONHCH_2CH_3$, $CONHCH_2CH_2CH_3$ and $CONHCH_2(CH_3)_2$, and a residue $R_3$ being selected from one of $COOCH_2CH_3$, $COOCH(CH_3)_2$, $CONHCH_2CH_3$, $CONHCH_2CH_2CH_3$ and $CONHCH_2(CH_3)_2$. The said derivative of 18β-glycyrrhetinic acid shows great efficiency in triggering the decrease of MMP, and inducing apoptosis in cancer cells through the generation of ROS and activation of p53, and which is capable of being used in pharmaceutical industry by manufacturing medication for suppressing cancer cell.

In the present invention, the derivatives of 18β-glycyrrhetinic acid are artificially synthesized from 18β-glycyrrhetinic acid which is but not limit to be extracted from particular plants or artificially synthesized.

Figure 1:
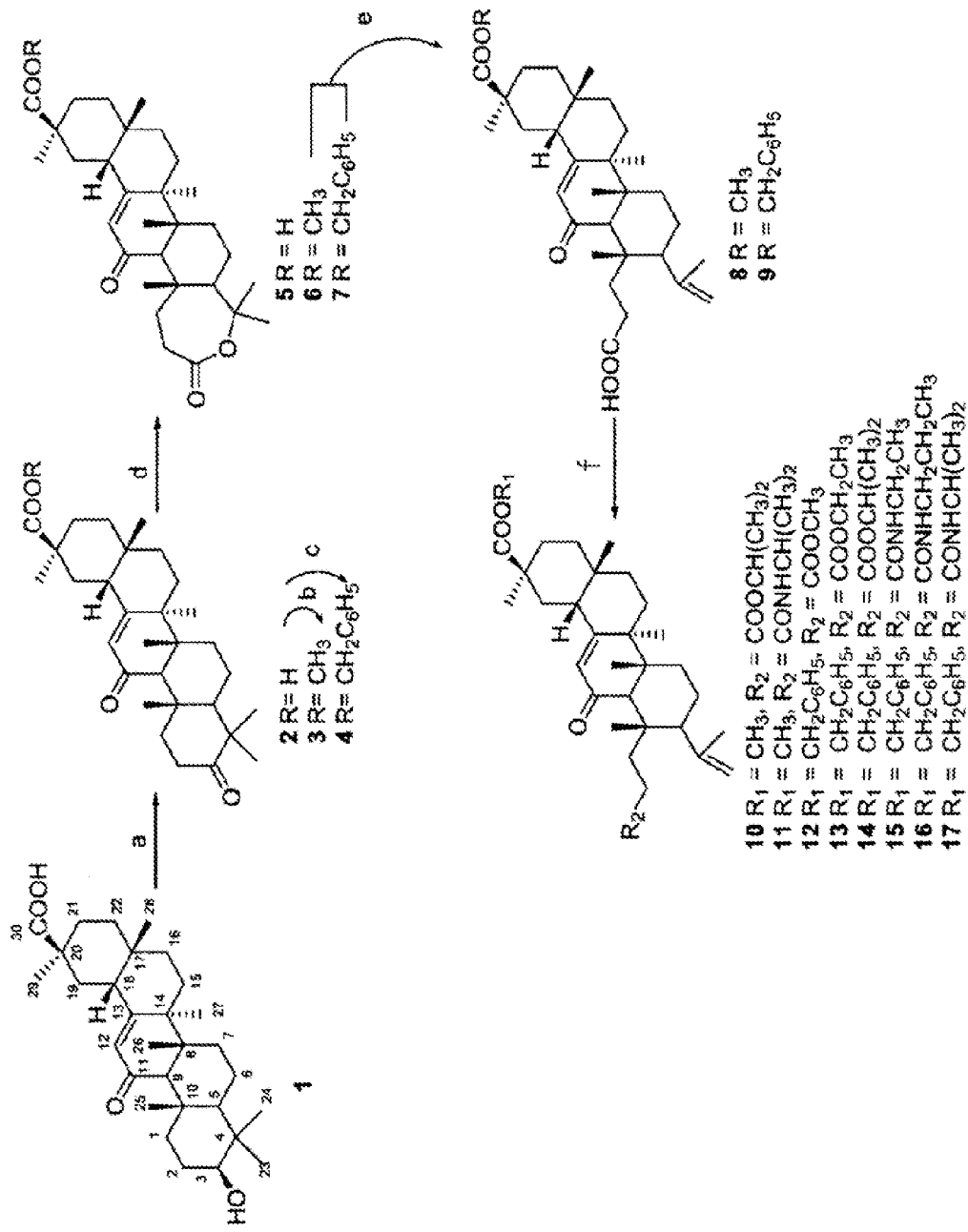
FIG. 1 is a diagram illustrating a preferable embodiment of the method for synthesizing the derivatives of 18β-glycyrrhetinic acid in the present invention.

Referring to FIG. 1, in accordance with a preferable embodiment of a method for synthesizing the derivatives of 18β-glycyrrhetinic acid in the present invention, 18β-glycyrrhetinic acid derivative of the present invention is prepared by a serial of processes including steps of (a) dissolving the 18β-glycyrrhetinic acid 1 in dimethyl formamide (DMF) to react with chromium trioxide ($CrO_3$) and to obtain a first compound, labeled as 2 in FIG. 1; (b/c) esterifying the first compound 2 with an alcohol to obtain a second compound comprising a residue C-30 of alkyl group; (d) lactonizing the second compound to obtain a third compound; (e) ring-opening a lactone ring of the third compound to obtain a forth compound, in the form of a seco-type; and (f) esterifying or carbamoylated the forth compound by reacting with alkyl group or amine group to obtain a fifth compound, namely being the derivatives of 18β-glycyrrhetinic acid of the present embodiment. Specifically, in the step of (a), the 18β-glycyrrhetinic acid is reacted with $CrO_3$ at room temperature for 12 hours to obtain the first compound 2 having a residue C-30 of hydrogen.

In a first case of the preferable embodiment, the step of (b) is carried out by conducting an esterfication of the first compound 2 with methanol ($CH_3OH$) and sulphuric acid ($H_2SO_4$) where reflux for 48 hours and, that thus the second compound comprising a residue C-30 of $CH_3$, being labeled as 3 in the FIG. 1, is obtain.

Next, the step of (d) of the first case is carried out by conducting lactonization of the second compound comprising a residue C-30 of $CH_3$ 3, to obtain the third compound comprising a residue C-30 of $CH_3$, being labeled as 6 in the FIG. 1. Specifically, in the step of (d) of the first case, the second compound 3 in 1.0 g, 21 mmol is dissolved in 30 ml of $CH_2Cl_2$ and reacted with m-chloroperoxybenzoic acid (m-CPBA), in 3.6 gram, 21.3 mmol for 12 hours, followed by diluting with chloroform, washing with 5% potassium iodide and 5% sodium thiosulfate, drying by sodium sulphate anhydrous and then concentrating the obtained third compound 6 as white solid.

Then, the step of (e) of the first case is processed by dissolving the third compound comprising a residue C-30 of $CH_3$ 6 in a solvent, such as isopropyl alcohol or dichloromethane, conducting a ring-opening reaction of the third compound 6 reacted with p-toluenesulfonic acid (p-TSA) to obtain the forth compound comprising a residue C-30 of $CH_3$ 8.

Finally, the step of (f) of the first case is carried out by conducting an esterification or carbamoylation of the forth compound comprising a residue C-30 of $CH_3$ 8, to obtain the fifth compound comprising a residue C-30 of $CH_3$, being labeled as 10, 11 in the FIG. 1. Precisely, in the step of (f) of the first case, a hydrogen in residue C-3 of COOH on the forth compound 8 is replaced by an alkyl group, such as halogenated alkanes including ethyl iodide or isopropyl iodide, or an amine, such as ethyl amine, propylamine or isopropyl amine, through the esterification or carbamoylation, in order to obtain the fifth compound 10, 11 being the derivatives of 18β-glycyrrhetinic acid in the present embodiment. The fifth compound 10, 11 of the present case can be 3,4-seco-11-oxo-18β-olean-4(23),12-dien-3,30-dioic acid 3-isopropyl 30-methyl, ester, or 3-isopropyl carbamoyl-11-oxo-18β-3,4-seco-olean-4(23),12-dien 30-methyl ester, respectively.

In an example of the step (f) in the present case, an esterfication of the forth compound 8, in 80 mg, 0.16 mmol, and isopropyl iodide is carried out under a performance of acetone and potassium carbonate, to obtain the 3,4-seco-11-oxo-18β-olean-4(23),12-dien-3,30-dioic acid 3-isopropyl 30-methyl, ester 10 as white amorphous powder. In the present example, the 3,4-seco-11-oxo-18β-olean-4(23),12-dien-3,30-dioic acid 3-isopropyl 30-methyl, ester 10 is obtained in a weight of 86.2 mg, 0.16 mmol, and with an efficiency of 100.0%: $[\alpha]^{25}_D$ 8 (c 0.1, CHCl$_3$). IR (film on NaCl)$^{-1}$ 1731, 1657. $^1$H NMR (CDCl$_3$): δ 0.82 (3H, s, Me-28), 1.15 (3H, s, Me-29), 1.16 (3H, s, Me-25), 1.17 (3H, s, Me-26), 1.21 (6H, d, J=6.4 Hz, —CH(CH$_3$)$_2$), 1.38 (3H, s, Me-27), 1.76 (3H, s, Me-24), 2.60 (1H, td, 13.4, 6.0 Hz, Hβ-18), 3.70 (3H, s, —OCH$_3$), 4.70 (1H, br s, H-23), 4.90 (1H, br s, H-23), 4.95 (1H, m, —CH(CH$_3$)$_2$), 5.69 (1H, s, H-12). See TABLE 1, $^{13}$C NMR (CDCl$_{13}$). EI-MS (70 eV) m/z (% rel. int.), 540 [M]$^+$ (63). HR-EI-MS m/z: calcd for C$_{34}$H$_{52}$O$_5$, 540.3815; found: 540.3814

In another example of the step (f) in the present case, a carbamoylation of the forth compound 8 in 212 mg, 0.43 mmol, and isopropyl amine is carried out under an activation of 1-ethyl-3-(3-dimethylaminopropyl)carbodiimide (EDCI) and the catalysis of 4-dimethylaminopyridine (DMAP), to obtain the 3-isopropyl carbamoyl-11-oxo-18β-3,4-seco-olean-4(23),12-dien 30-methyl ester 11 as white amorphous powder. In the present example, the 3-isopropyl carbamoyl-11-oxo-18β-3,4-seco-olean-4(23), 12-dien 30-methyl ester 11 is obtained in a weight of 201.6 mg, 0.37 mmol, and with an efficiency of 86.0%: $[\alpha]^{25}_D$ 10 (c 0.1, CHCl$_3$). IR (film on NaCl) cm$^{-1}$ 3299, 1727, 1661. $^1$H NMR (CDCl$_3$) δ 0.81 (3H, s, Me-28), 1.10 (3H, d, J=6.8 Hz, —CH(CH$_3$)(CH$_3$)), 1.11 (3H, d, J=6.8 Hz, —CH(CH$_3$)(CH$_3$)), 1.14 (6H, s, Me-26 and 29), 1.17 (3H, s, Me-25), 1.37 (3H, s, Me-27), 1.77 (3H, s, Me-24), 2.47 (1H, td, J=13.2, 6.0 Hz, Hβ-18), 3.69 (3H, s, OCH$_3$), 4.01 (1H, m, —CH(CH$_3$)$_2$), 4.73 (1H, br s, H-23), 4.90 (1H, br s, H-23), 5.48 (1H, d, J=7.6 Hz, NH), 5.69 (1H, s, H-12). See TABLE 1, $^{13}$C NMR (CDCl$_3$). EI-MS (70 eV) m/z (% rel. int.), 539 [M]$^+$ (70). HR-EI-MS m/z calcd for C$_{34}$H$_{53}$NO$_4$, 539.3974; found: 539.3956

Furthermore, with reference to FIG. 1 either, in a second case of the preferable embodiment, the step of (c) is processed by conducting an esterfication of the first compound 2 with benzyl alcohol (C$_6$H$_5$CH$_2$OH) in dichloromethane (CH$_2$Cl$_2$) and DMAP under an activation of EDCl, and obtaining the second compound comprising a residue C-30 of benzyl alcohol, as been labeled to 4 in the FIG. 1.

Likewise, the step of (d) of the second case is processed by conducting an lactonization of the second compound comprising a residue C-30 of benzyl ester 4, to obtain the third compound comprising a residue C-30 of benzyl ester being labeled as 7 in the FIG. 1. Specifically, in the step of (d) of the second case, the second compound 4 is dissolved in dichloromethane at first, and carried out a lactonization by reacting with m-CPBA at room temperature for 12 hours, to obtain the third compound 7 of the second case.

As following, in the step of (e) of the second case, the third compound comprising a residue C-30 of benzyl ester 7 is dissolved in a solvent, such as isopropyl alcohol or dichloromethane, and conducted a ring-opening reaction of the third compound comprising a residue C-30 of benzyl ester 7 with a reacting with of p-TSA, to obtain the forth compound comprising a residue C-30 of benzyl ester 9.

Finally, the step of (f) of the second case is carried out by conducting an esterfication or a carbamoylation of the forth compound comprising a residue C-30 of benzyl ester 9, to obtain the fifth compound comprising a residue C-30 of benzyl ester, being the derivatives of 18β-glycyrrhetinic acid in the present embodiment and with labels of 12, 13, 14, 15, 16, and 17. Precisely, in the step of (f) of the second case, a hydrogen in the residue of C-3 of COOH of the forth compound 9 is replaced by an alkyl group, such as halogenated alkanes including ethyl iodide or isopropyl iodide, or an amine group, such as ethyl amine, propylamine or isopropyl amine, through the esterification or carbomoylation, in order to obtain the fifth compound being 3,4-seco-11-oxo-18β-olean-4(23), 12-dien-3,30-dioic acid 3-methyl-30-benzyl ester 12, 3,4-seco-11-oxo-18β-olean-4(23),12-dien-3,30-dioic acid 3-ethyl,30-benzyl ester 13, 3,4-seco-1'-oxo-18β-olean-4(23),12-dien-3,30. dioic acid 3-isopropyl-30-benzyl ester 14, 3-ethyl carbamoyl-11-oxo-18β-3,4-seco-olean-4(23),12-dien-30-benzyl ester 15, 3-propylcarbamoyl-11-oxo-18β-3,4-seco-olean-4(23),12-dien 30-benzyl ester 16, and 3-isopropylcarbamoyl-11-oxo-18β-3,4-seco-olean-4(23), 12-dien 30-benzyl ester 17 respectively, as they are shown in the FIG. 1.

As a first example of the step (f) in the second case, an esterfication of the forth compound 9 in 112 mg, 0.20 mmol, and ethyl iodide is carried out under a performance of acetone and potassium carbonate, to obtain the 3,4-seco-11-oxo-18β-olean-4(23),12-dien-3,30-dioic acid 3-ethyl,30-benzyl ester 13 as white amorphous powder. In the present example, the 3,4-seco-11-oxo-18β-olean-4(23),12-dien-3,30-dioic acid 3-ethyl,30-benzyl ester 13 is obtained in a weight of 81.6 mg, 0.13 mmol, and with an efficiency of 65.0%: $[\alpha]^{25}_D$ 3 (c 0.5, CHCl$_3$). IR (film on NaCl) cm$^{-1}$ 1727, 1657, 1579. $^1$H NMR (CDCl$_3$) δ 0.74 (3H, s, Me-28), 1.15 (3H, s, Me-29), 1.16 (6H, s, Me-25 and 26), 1.22 (3H, t, J=7.2 Hz, —CH$_2$CH$_3$), 1.37 (3H, s, Me-27), 1.75 (3H, s, Me-24), 2.60 (1H, td, J=13.2, 6.0 Hz, Hβ-18), 4.10 (2H, q, J=7.2 Hz, —CH$_2$CH$_3$), 4.69 (1H, br s, H-23), 4.90 (1H, br s, H-23), 5.09 (1H, 8, J=12.4 Hz, —OCHH—), 5.20 (1H, 8, J=12.0 Hz, —OCHH—), 5.57 (1H, s, H-12), 7.37 (5H, m, aromatic proton). See TABLE 1, $^{13}$C NMR (CDCl$_3$). EI-MS (70 eV) m/z (% rel. int.), 602 [M]$^+$ (21). HR-EI-MS m/z calcd for C$_{39}$H$_{54}$O$_5$, 602.3971; found: 602.3971

As a second example of the step (f) in the second case, an esterfication of the forth compound 9 in 100 mg, 0.17 mmol, and isopropyl iodide is carried out under a performance of acetone and potassium carbonate, to obtain the 3,4-seco-11-oxo-18β-olean-4(23),12-dien-3,30. dioic acid 3-isopropyl-30-benzyl ester 14 as white amorphous powder. In the present example, the 3,4-seco-11-oxo-18β-olean-4(23),12-dien-3, 30. dioic acid 3-isopropyl-30-benzyl ester 14 is obtained in a weight of 49.4 mg, 0.08 mmol, and with an efficiency of 47.1%: $[\alpha]^{25}_D$ 16 (c 0.05, CHCl$_3$). IR (film on NaCl) cm$^{-1}$ 1727, 1657, 1631. $^1$H NMR (CDCl$_3$) δ 0.74 (3H, s, Me-28), 1.15 (3H, s, Me-29), 1.16 (6H, s, Me-25 and 26), 1.19 (6H, d, J=6.4 Hz, —CH(CH$_3$)$_2$), 1.39 (3H, s, Me-27), 1.76 (3H, s, Me-24), 2.58 (1H, td, J=13.2, 6.4 Hz, Hβ-18), 4.69 (1H, br s, H-23), 4.90 (1H, br s, H-23), 4.95 (1H, m, —CH(CH$_3$)$_2$), 5.09 (1H, d, J=12.4 Hz, —OCHH—), 5.20 (1H, d, J=12.4 Hz, —OCHH—), 5.57 (1H, s, H-12), 7.38 (5H, m, aromatic proton). See TABLE 1, $^{13}$C NMR (CDCl$_3$). EI-MS (70 eV) m/z (% rel. int.), 616 [M]$^+$ (33). HR-EI-MS m/z calcd for C$_{40}$H$_{56}$O$_5$, 616.4127; found: 616.4136

As a third example of the step (f) in the second case, an esterfication of the forth compound 9 in 100 mg, 0.17 mmol, and ethyl amine is carried out under activation of EDCI and the catalysis of DMAP, to obtain the 3-ethyl carbamoyl-11-oxo-18β-3,4-seco-olean-4(23),12-dien-30-benzyl ester 15 as white amorphous powder. In the present example, the 3-Ethyl carbamoyl-11-oxo-18β-3,4-seco-olean-4(23),12-dien-30-benzyl ester 15 is obtained in a weight of 58.0 mg, 0.097 mmol, and with an efficiency of 57.1%: $[\alpha]^{25}{}_D$ 11 (c 0.35, CHCl$_3$). IR (film on NaCl) cm$^{-1}$ 3299, 1727, 1657, 1553. $^1$H NMR (CDCl$_3$) δ 0.75 (3H, s, Me-28), 1.10 (3H, t, J=7.2 Hz, —CH$_2$CH$_3$), 1.14 (3H, s, Me-29), 1.15 (3H, s, Me-25), 1.16 (3H, s, Me-26), 1.36 (3H, s, Me-27), 1.77 (3H, s, Me-24), 2.49 (1H, td, J=13.2, 6.0 Hz, Hβ-18), 3.23 (2H, m, —CH$_2$CH$_3$), 4.74 (1H, br s, H-23), 4.90 (1H, br s, H-23), 5.09 (1H, d, J=12.0 Hz, —OCHH—), 5.20 (1H, d, J=12.0 Hz, —OCHH—), 5.58 (1H, s, H-12), 5.67 (1H, br s, NH), 7.36 (5H, m, aromatic proton). See TABLE 1, $^{13}$C NMR (CDCl$_3$). EI-MS (70 eV) m/z (% rel. int.), 601 [M]$^+$ (36). HR-EI-MS m/z calcd for C$_{39}$H$_{55}$NO$_4$, 601.4131; found: 601.4131

As a forth example of the step (f) in the second case, an esterification of the forth compound 9 in 125 mg, 0.22 mmol, and propylamine is carried out under activation of EDCI and the catalysis of DMAP, to obtain the 3-propylcarbamoyl-11-oxo-18β-3,4-seco-olean-4(23),12-dien 30-benzyl ester 16 as white amorphous powder. In the present example, 3-propyl-carbamoyl-11-oxo-18β-3,4-seco-olean-4(23),12-dien 30-benzyl ester 16 is obtained in a weight of 58.0 mg, 0.097 mmol, and with an efficiency of 57.1%: $[\alpha]^{25}{}_D$ 15 (c 0.5, CHCl$_3$). IR (film on NaCl) cm$^{-1}$ 3439, 1724, 1657, 1513. $^1$H NMR (CDCl$_3$) δ 0.75 (3H, s, Me-28), 0.90 (3H, t, J=7.6 Hz, —CH$_2$CH$_2$CH$_3$), 1.14 (3H, s, Me-29), 1.15 (3H, s, Me-25), 1.16 (3H, s, Me-26), 1.36 (3H, s, Me-27), 1.49 (2H, q, J=7.2 Hz, —CH$_2$CH$_2$CH$_3$), 1.77 (3H, s, Me-24), 2.49 (1H, td, J=13.2, 6.0 Hz, Hβ-18), 3.16 (2H, dd, J=13.6, 6.0 Hz, —CH$_2$CH$_2$CH$_3$), 4.74 (1H, br s, H-23), 4.90 (1H, br s, H-23), 5.09 (1H, d, J=12.4 Hz, —OCHH—), 5.20 (1H, d, J=12.4 Hz, —OCHH—), 5.73 (1H, br s, NH), 5.58 (1H, s, H-12), 7.36 (5H, m, aromatic proton). See TABLE 1, $^{13}$C NMR (CDCl$_3$). EI-MS (70 eV) m/z (% rel. int.), 615 [M]$^+$ (36). HR-EI-MS m/z calcd for C$_{40}$H$_{57}$NO$_4$, 615.4287; found: 615.4283

As a fifth example of the step (f) in the second case, an esterification of the forth compound 9 in 100 mg, 0.17 mmol, and isopropyl amine is carried out under activation of EDCI and the catalysis of DMAP, to obtain the 3-isopropylcarbamoyl-11-oxo-18β-3,4-seco-olean-4(23), 12-dien 30-benzyl ester 17 as white amorphous powder. In the present example, 3-isopropylcarbamoyl-11-oxo-18β-3,4-seco-olean-4(23), 12-dien 30-benzyl ester 17 is obtained in a weight of 58.0 mg, 0.097 mmol, and with an efficiency of 57.1%: $[\alpha]^{25}{}_D$ 7 (c 0.25, CHCl$_3$). IR (film on NaCl) cm$^{-1}$ 3306, 1727, 1657, 1535. $^1$H NMR (CDCl$_3$) δ 0.75 (3H, s, Me-28), 1.10 (3H, d, J=6.8 Hz, —CH(CH$_3$)(CH$_3$)), 1.12 (3H, d, J=6.8 Hz, —CH(CH$_3$)(CH$_3$)), 1.14 (3H, s, Me-29), 1.15 (3H, s, Me-25), 1.16 (3H, s, Me-26), 1.36 (3H, s, Me-27), 1.77 (3H, s, Me-24), 2.46 (1H, td, J=13.2, 6.0 Hz, Hβ-18), 4.00 (1H, m, —CH(CH$_3$)$_2$), 4.74 (1H, br s, H-23), 4.91 (1H, br s, H-23), 5.09 (1H, d, J=12.4 Hz, —OCHH—), 5.20 (1H, d, J=12.4 Hz, —OCHH—), 5.56 (1H, br s, NH), 5.58 (1H, s, H-12), 7.36 (5H, m, aromatic proton). See TABLE 1, $^{13}$C NMR (CDCl$_3$). EI-MS (70 eV) m/z (% rel. int.), 615 [M]$^+$ (42). HR-EI-MS m/z calcd for C$_{40}$H$_{57}$NO$_4$, 615.4288; found: 615.4286

Figure 2:
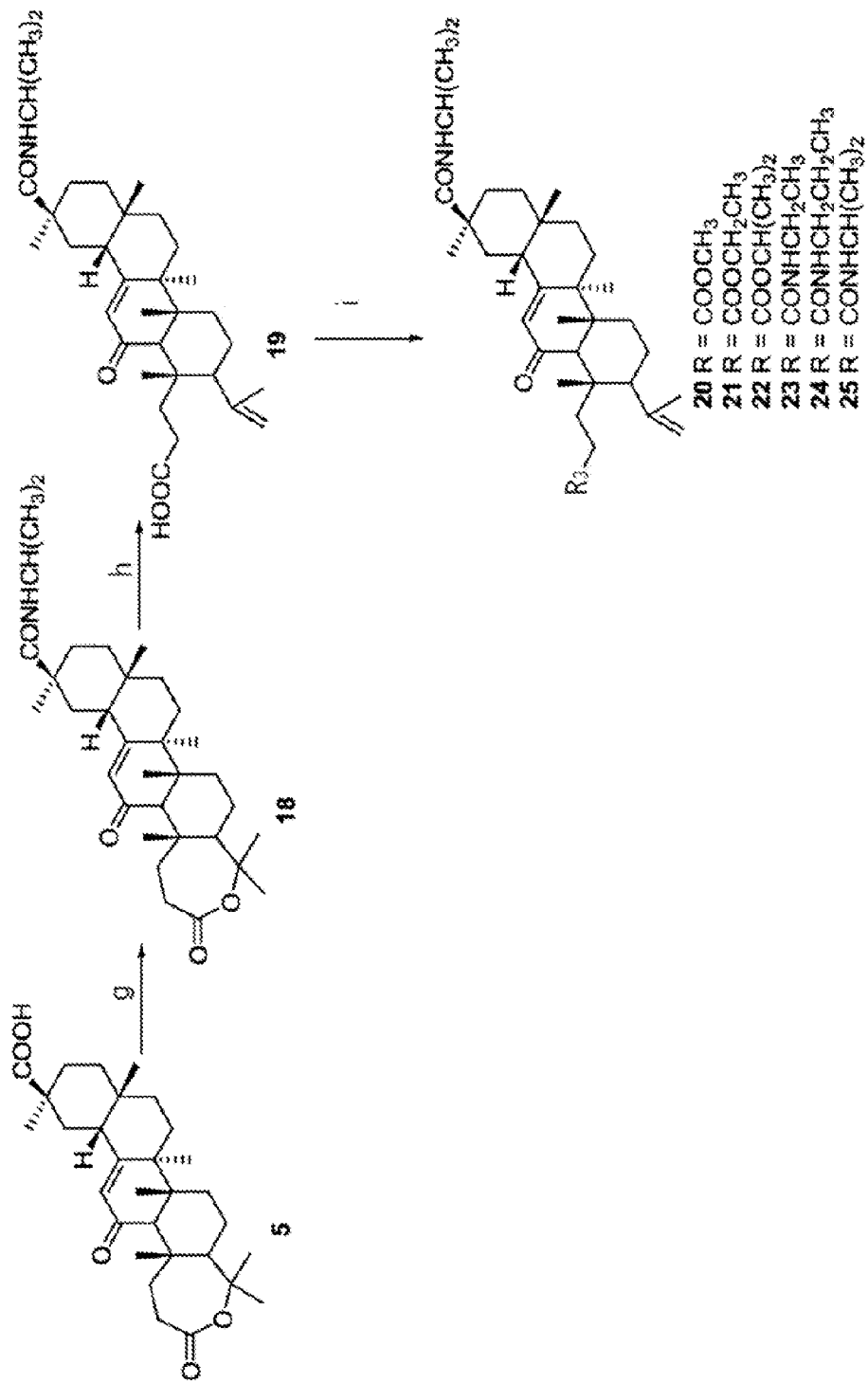
FIGS. 2 and 3 are diagrams illustrating another preferable embodiment of method for synthesizing the derivatives of 18β-glycyrrhetinic acid in the present invention.
Figure 3:
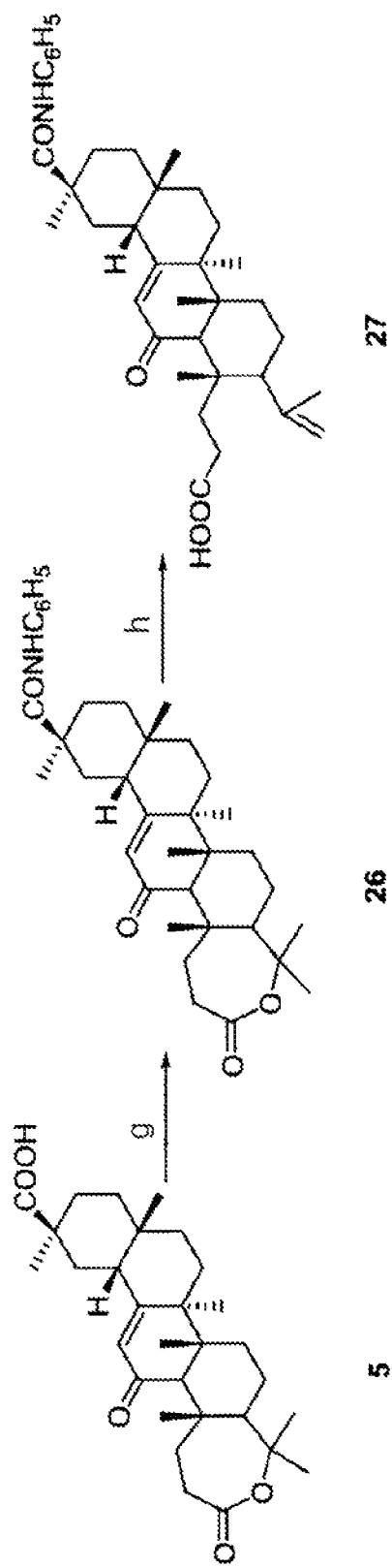

In FIGS. 2 and 3, in accordance with another preferable embodiment of the method for synthesizing the derivatives of 18β-glycyrrhetinic acid of the present invention, a derivative of 18β-glycyrrhetinic acid labeled as 5 is prepared and dissolved in dichloromethane (CH$_2$Cl$_2$), accompanied by sequentially undergoing a serial of processes including steps of: (g) carbumoylating the derivative of 18β-glycyrrhetinic acid 5 with an amine to obtain a sixth compound having a carbamoyl group; (h) ring-opening a lactone ring of the sixth compound to obtain a seventh compound in a form of seco-type and having a carbamoyl group; and (i) esterifying or carbumoylating of the seventh compound to obtain an eighth compound comprising a carbamoyl group or alkyl group on a residue C-3, wherein the eighth compound is the derivatives of 18β-glycyrrhetinic acid of the present embodiment.

In a first case of the present embodiment, the step of (g) is carried out by conducting a carbamoylation of the derivative of 18β-glycyrrhetinic acid 5 and isopropyl amine solution comprising DMAP under an activation of EDCI, and thus the sixth compound comprising a residue C-30 of a carbamoyl group, being label as 18 in the FIG. 2 is obtained.

Next, the step of (h) of the first case is processed by dissolving the sixth compound 18 in a solvent, such as dichloromethane, and conducting a ring-opening reaction of the sixth compound 18 with a performance of p-TSA, to obtain the seventh compound in a form of sero-type and comprising a residue C-30 of a carbamoyl group, being label as 19. Specifically, the sixth compound 18, in 1.0 g, 2.01 mmol, is dissolved in 30 ml dichloromethane in the present case.

Finally, the step of (i) in the first case is processed by dissolving the seventh compound 19 in acetone or CH$_2$Cl$_2$ and carrying out an esterification or a carbamoylation of the seventh compound 19 to obtain an eighth compound comprising a residue C-30 of carbamoyl or alkyl group, labeled as 20, 21, 22, 23, 24, and 25 in the FIG. 2, being the derivatives of 18β-glycyrrhetinic acid of the present embodiment. Precisely, in the step of (i), the esterification of the seventh compound 19 is conducted with potassium carbonate (K$_2$CO$_3$) and a halogenated alkane also dissolved in acetone, such as ethyl iodide and isopropyl iodide, to obtain 30-Isopropylcarbamoyl-11-oxo-18β-3,4-seco-olean-4(23),12-diene 3-methyl ester 20, 30-isopropyl carbamoyl-11-oxo-18β-3,4-seco-olean-4(23),12-dien 3-ethyl ester 21, 30-isopropyl carbamoyl-11-oxo-18β-3,4-seco-olean-4(23),12-dien 3-isopropyl ester 22. Yet, the carbamoylation of the seventh compound 19 is conducted with an amine dissolved in EDCI and DMAP, such as ethyl amine, propyl amine and isopropylamine, to obtain 30-isopropylcarbamoyl-11-oxo-18β-3,4-seco-olean-4(23), 12-dien 3-ethyl carbamate 23, 30-isopropyl carbamoyl-11-oxo-18β-3,4-seco-olean-4(23), 12-dien 3-propyl carbamate 24, and 3,4-seco-11-oxo-18β-olean-4 (23),12-dien-3,30-diisopropyl carbamate 25.

In a first example of the step (i) in the present case, an esterification of the eighth compound 19 in 100 mg, 0.19 mmol and ethyl iodide is carried out under a catalysis of potassium carbonate, to obtain the 30-isopropyl carbamoyl-11-oxo-18β-3,4-seco-olean-4(23),12-dien 3-ethyl ester 21 as white amorphous powder. In the present example, the 30-isopropyl carbamoyl-11-oxo-18β-3,4-seco-olean-4(23),12-dien 3-ethyl ester 21 is obtained in a weight of 27.3 mg, 0.049 mmol, and with an efficiency of 25.8%: $[\alpha]^{25}{}_D$ 9 (c 0.25, CHCl$_3$). IR (film on NaCl) cm$^{-1}$ 3365, 1735, 1650. $^1$H NMR (CDCl$_3$): δ 0.82 (3H, s, Me-28), 1.11 (3H, s, Me-26), 1.14 (3H, d, J=6.4 Hz, —CH(CH$_3$)(CH$_3$)), 1.16 (3H, s, Me-25), 1.16 (3H, d, J=6.4 Hz, —CH(CH$_3$)(CH$_3$)), 1.17 (3H, s, Me-29), 1.23 (3H, t, J=7.2 Hz, —CH$_2$CH$_3$), 1.39 (3H, s, Me-27), 1.76 (3H, s, Me-24), 2.61 (1H, td, J=13.2, 6.4 Hz, Hβ-18), 4.08 (2H, q, J=7.2 Hz, —CH$_2$CH$_3$), 4.12 (1H, m, —CH(CH$_3$)$_2$) 4.70 (1H, br s, H-23), 4.90 (1H, br s, H-23), 5.33 (1H, d, J=8.0 Hz, NH), 5.65 (1H, s, H-12). See TABLE 1, $^{13}$C NMR (CDCl$_3$). EI-MS (70 eV) m/z (% rel. int.): 553 [M]$^+$ (62). HR-EI-MS m/z: C$_{35}$H$_{55}$NO$_4$, 553.4131; found: 553.4133

In a second example of the step (i) in the present case, an esterification of the eighth compound 19 in 80 mg, 0.15 mmol and isopropyl iodide is carried out under a catalysis of potassium carbonate, to obtain the 30-isopropyl carbamoyl-11-oxo-18β-3,4-seco-olean-4(23),12-dien 3-isopropyl ester 22 as white amorphous powder. In the present example, the 30-isopropyl carbamoyl-11-oxo-18β-3,4-seco-olean-4(23), 12-dien 3-isopropyl ester 22 is obtained in a weight of 73.3 mg, 0.13 mmol, and with an efficiency of 86.7%: $[\alpha]^{25}_D$ 1 (c 1.0, CHCl$_3$). IR (film on NaCl) cm$^{-1}$ 3373, 1727, 1661. $^1$H NMR (CDCl$_3$), δ 0.82 (3H, s, Me-28), 1.11 (3H, s, Me-29), 1.14 (3H, d, J=6.8 Hz, —CH(CH$_3$)(CH$_3$)), 1.16 (3H, s, Me-25), 1.16 (3H, d, J=6.8 Hz, —CH(CH$_3$)(CH$_3$)), 1.17 (3H, s, Me-26), 1.20 (6H, d, J=6.4 Hz, —CH(CH$_3$)$_2$), 1.39 (3H, s, Me-27), 1.76 (3H, s, Me-24), 2.59 (1H, td, J=13.2, 6.4 Hz, Hβ-18), 4.12 (1H, m, —CH(CH$_3$)$_2$), 4.69 (1H, br s, H-23), 4.90 (1H, br s, H-23), 4.95 (1H, m, —CH(CH$_3$)$_2$), 5.34 (1H, d, J=8.0 Hz, NH), 5.64 (1H, s, H-12). See TABLE 1 $^{13}$C NMR (CDCl$_3$). EI-MS (70 eV) m/z (% rel. int.), 567 [M]$^+$ (64). HR-EI-MS m/z calcd for C36H57NO4, 567.4288; found: 567.4269

In a third example of the step (i) in the present case, a carbamoylation of the eighth compound 19 in 100 mg, 0.19 mmol and ethyl amine is carried out under catalysis of DMAP and activation of EDCI, to obtain the 30-isopropylcarbamoyl-11-oxo-18β-3,4-seco-olean-4(23), 12-dien 3-ethyl carbamate 23 as white amorphous powder. In the present example, the 30-isopropylcarbamoyl-11-oxo-18β-3,4-seco-olean-4 (23), 12-dien 3-ethyl carbamate 23 is obtained in a weight of 59.3 mg, 0.11 mmol, and with an efficiency of 58.0%: $[\alpha]^{25}_D$ 22 (c 0.25, CHCl$_3$). IR (film on NaCl) cm$^{-1}$ 3292, 1731, 1653. $^1$H NMR (CDCl$_3$) δ 0.82 (3H, s, Me-28), 1.10 (3H, t, J=7.2 Hz, —CH$_2$CH$_3$), 1.11 (3H, s, Me-26), 1.15 (3H, d, J=6.8 Hz, —CH(CH$_3$)(CH$_3$)), 1.16 (3H, d, J=6.8 Hz, —CH(CH$_3$)(CH$_3$)), 1.16 (3H, s, Me-25), 1.17 (3H, s, Me-29), 1.39 (3H, s, Me-27), 2.51 (1H, td, J=13.2, 6.0 Hz, Hβ-18), 3.23 (2H, m, —CH$_2$CH$_3$), 4.12 (1H, m, —CH(CH$_3$)$_2$), 4.74 (1H, br s, H-23), 4.90 (1H, br s, H-23), 5.34 (1H, t, J=8.4 Hz, NH), 5.68 (1H, t, J=4.0 Hz, —NHCH$_2$CH$_3$), 5.68 (1H, s, H-12). See TABLE 1, $^{13}$C NMR (CDCl$_3$). EI-MS (70 eV) m/z (% rel. int.), 552 [M]$^+$ (47). HR-EI-MS m/z calcd for C$_{35}$H$_{36}$N$_2$O$_3$, 552.4291; found: 552.4288

In a forth example of the step (i) in the present case, a carbamoylation of the eighth compound 19 in 100 mg, 0.19 mmol and propyl amine is carried out under catalysis of DMAP and activation of EDCI, to obtain the 30-isopropyl carbamoyl-11-oxo-18β-3,4-seco-olean-4(23), 12-dien 3-propyl carbamate 24 as white amorphous powder. In the present example, the 30-isopropyl carbamoyl-11-oxo-18β-3, 4-seco-olean-4(23), 12-dien 3-propyl carbamate 24 is obtained in a weight of 46.1 mg, 0.08/1 mmol, and with an efficiency of 42.6%: $[\alpha]^{25}_D$ 4(c 0.25, CHCl$_3$). IR (film on NaCl) cm$^{-1}$ 3424, 1735, 1653. $^1$H NMR (CDCl$_3$) δ 0.83 (3H, s, Me-28), 0.91 (3H, t, J=7.2 Hz, —CH$_2$CH$_2$CH$_3$), 1.11 (3H, s, Me-26), 1.15 (3H, d, J=6.8 Hz, —CH(CH$_3$)(CH$_3$)), 1.16 (3H, d, J=6.8 Hz, —CH(CH$_3$)(CH$_3$)), 1.16 (3H, s, Me-25), 1.17 (3H, s, Me-29), 1.38 (3H, s, Me-27), 1.77 (3H, s, Me-24), 2.23 (2H, m, —CH$_2$CH$_2$CH$_3$), 2.51 (1H, td, J=13.2, 6.0 Hz, Hβ-18), 3.16 (2H, dd, J=13.2, 6.4 Hz, —CH$_2$CH$_2$CH$_3$), 4.12 (1H, m, —CH(CH$_3$)$_2$), 4.74 (1H, br s, H-23), 4.91 (1H, br s, H-23), 5.33 (1H, d, J=8.4 Hz, NH), 5.67 (1H, s, H-12), 5.68 (1H, t, J=4.0 Hz, —NHCH$_2$CH$_2$CH$_3$) $^{13}$C NMR (CDCl$_3$) (See TABLE 1). EI-MS (70 eV) m/z (% rel. int.), 566 [m]$^+$ (95). HR-EI-MS m/z calcd for C36H58N2O3, 566.4447; found: 566.4439

In a forth example of the step (i) in the present case, the carbamoylation of the eighth compound 19 in 100 mg, 0.19 mmol and isopropylamine is carried out under catalysis of DMAP and activation of EDCI, to obtain the 3,4-seco-11-oxo-18β-olean-4(23),12-dien-3,30-diisopropyl carbamate 25 as white amorphous powder. In the present example, the 3,4-seco-11-oxo-18β-olean-4(23),12-dien-3,30-diisopropyl carbamate 25 is obtained in a weight of 61.4 mg, 0.11 mmol, and with an efficiency of 58.0%: $[\alpha]^{25}_D$4(c 0.25, CHCl$_3$). IR (film on NaCl) cm$^{-1}$ 3439, 1727, 1650. $^1$H NMR (CDCl$_3$) δ 0.80 (3H, s, Me-28), 1.11 (3H, s, Me-26), 1.12 (6H, d, J=6.8 Hz, —CH(CH$_3$)$_2$), 1.15 (3H, s, Me-29), 1.15 (6H, d, J=6.8 Hz, —CH(CH$_3$)$_2$), 1.17 (3H, s, Me-25), 1.38 (3H, s, Me-27), 1.79 (3H, s, Me-24), 2.48 (1H, td, J=13.2, 6.4 Hz, Hβ-18), 4.02 (1H, m, —CH(CH$_3$)$_2$), 4.12 (1H, m, —CH(CH$_3$)$_2$), 4.74 (1H, br s, H-23), 4.90 (1H, br s, H-23), 5.34 (1H, d, J=7.6 Hz, NH), 5.46 (1H, d, J=7.6 Hz, NH), 5.65 (1H, s, H-12). See TABLE 1, $^{13}$C NMR (CDCl$_3$). EI-MS (70 eV) m/z (% rel. int.), 566 [M]$^+$ (89). HR-EI-MS m/z calcd for C36H58N2O3, 566.4447; found: 566.4444

In a second case of the present embodiment, the step of (g) is carried out by conducting a carbamoylation of the derivative of 18β-glycyrrhetinic acid 5 and alkyl solution comprising DMAP under an activation of EDCI, and thus the sixth compound comprising a residue C-30 of an alkyl group, being label as 26 in the FIG. 3 is obtained.

Next, the step of (h) of the second case is processed by dissolving the sixth compound 26 in a solvent, such as dichloromethane, and conducting a ring-opening reaction of the sixth compound 26 with performance of p-TSA, to obtain a seventh compound in a form of sero-type and comprising a residue C-30 of a phenylcarbamoyl group, being label as 27, wherein the seventh compound 27 is one of the derivatives of 18β-glycyrrhetinic acid of the present embodiment. Specifically, the sixth compound 26 in 1.0 g, 1.7 mmol is dissolved in 30 ml dichloromethane in the present case.

TABLE 1

| residue | 10 | 11 | 13 | 14 | 15 | 16 | 17 | 21 | 22 | 23 | 24 | 25 |
|---|---|---|---|---|---|---|---|---|---|---|---|---|
| | \multicolumn{12}{c}{$^{13}$C NMR spectroscopic data for compounds of 10, 11, 13-17 and 21-25} |
| C-1 | 23.5 | 23.8 | 23.8 | 23.8 | 23.8 | 23.8 | 23.8 | 23.8 | 23.8 | 23.8 | 23.8 | 23.8 |
| C-2 | 31.4 | 32.2 | 31.4 | 31.4 | 32.0 | 32.0 | 32.1 | 31.4 | 31.4 | 32.0 | 32.1 | 32.1 |
| C-3 | 173.4 | 172.4 | 173.9 | 173.4 | 173.2 | 173.2 | 172.3 | 174.6 | 173.4 | 173.2 | 173.3 | 172.4 |
| C-4 | 146.6 | 146.6 | 146.6 | 146.6 | 146.6 | 146.6 | 146.6 | 146.5 | 146.5 | 146.6 | 146.6 | 146.6 |
| C-5 | 38.8 | 39.0 | 38.7 | 38.8 | 39.0 | 39.0 | 39.0 | 38.8 | 38.8 | 39.0 | 39.0 | 39.0 |
| C-6 | 29.7 | 31.1 | 28.4 | 29.7 | 31.3 | 31.3 | 31.1 | 28.6 | 29.7 | 29.5 | 29.5 | 29.5 |
| C-7 | 34.3 | 35.7 | 34.4 | 34.3 | 35.6 | 35.7 | 35.6 | 34.4 | 34.3 | 35.6 | 35.7 | 35.7 |
| C-8 | 43.6 | 43.7 | 44.0 | 44.0 | 44.0 | 44.0 | 44.0 | 43.3 | 43.3 | 43.3 | 43.3 | 43.3 |
| C-9 | 52.8 | 53.1 | 52.8 | 52.7 | 53.0 | 53.1 | 53.1 | 52.8 | 52.8 | 53.1 | 53.0 | 53.0 |
| C-10 | 41.2 | 41.2 | 41.2 | 41.2 | 41.2 | 41.2 | 41.2 | 42.2 | 42.1 | 42.0 | 41.2 | 41.2 |
| C-11 | 199.6 | 200.4 | 199.5 | 199.5 | 200.4 | 200.4 | 200.3 | 199.6 | 199.5 | 200.3 | 200.3 | 200.3 |
| C-12 | 128.5 | 128.4 | 128.2 | 128.3 | 128.2 | 128.2 | 128.2 | 128.4 | 128.4 | 128.4 | 128.4 | 128.4 |
| C-13 | 169.3 | 170.3 | 169.2 | 169.1 | 170.2 | 170.3 | 170.2 | 169.5 | 169.4 | 170.4 | 170.4 | 170.3 |
| C-14 | 45.1 | 45.0 | 45.0 | 45.0 | 45.0 | 45.0 | 45.0 | 45.0 | 45.0 | 45.0 | 45.0 | 45.0 |
| C-15 | 26.4 | 26.4 | 26.4 | 26.4 | 26.3 | 26.3 | 26.3 | 26.4 | 26.4 | 26.4 | 26.4 | 26.4 |

TABLE 1-continued

¹³C NMR spectroscopic data for compounds of 10, 11, 13-17 and 21-25

| residue | 10 | 11 | 13 | 14 | 15 | 16 | 17 | 21 | 22 | 23 | 24 | 25 |
|---|---|---|---|---|---|---|---|---|---|---|---|---|
| C-16 | 26.5 | 26.5 | 26.5 | 26.5 | 26.5 | 26.5 | 26.5 | 26.5 | 26.5 | 26.6 | 26.6 | 26.6 |
| C-17 | 31.8 | 31.8 | 31.7 | 31.7 | 31.7 | 31.7 | 31.7 | 31.9 | 31.9 | 31.9 | 31.9 | 31.9 |
| C-18 | 48.4 | 48.3 | 48.1 | 48.1 | 48.2 | 48.2 | 48.2 | 48.2 | 48.2 | 48.1 | 48.1 | 48.1 |
| C-19 | 41.2 | 41.2 | 43.6 | 43.6 | 43.7 | 43.7 | 43.7 | 43.7 | 41.1 | 41.1 | 41.1 | 41.1 |
| C-20 | 44.0 | 44.0 | 50.7 | 50.6 | 50.9 | 51.0 | 51.0 | 43.7 | 43.7 | 43.8 | 43.8 | 43.7 |
| C-21 | 31.1 | 31.3 | 31.2 | 31.2 | 31.1 | 31.1 | 31.2 | 31.5 | 31.4 | 31.5 | 31.5 | 31.5 |
| C-22 | 37.7 | 37.7 | 37.7 | 37.7 | 37.6 | 37.6 | 37.6 | 37.4 | 37.4 | 37.4 | 37.4 | 37.4 |
| C-23 | 114.2 | 114.3 | 114.2 | 114.2 | 114.3 | 114.3 | 114.3 | 114.2 | 114.2 | 114.4 | 114.3 | 114.3 |
| C-24 | 23.8 | 23.5 | 23.5 | 23.5 | 23.5 | 23.5 | 23.5 | 23.8 | 23.5 | 23.5 | 23.5 | 23.5 |
| C-25 | 19.5 | 19.5 | 19.5 | 19.5 | 19.5 | 19.5 | 19.4 | 19.5 | 19.5 | 19.6 | 19.6 | 19.5 |
| C-26 | 18.6 | 18.7 | 18.4 | 18.6 | 18.7 | 18.7 | 18.7 | 18.7 | 18.6 | 18.7 | 18.7 | 18.7 |
| C-27 | 23.4 | 23.5 | 23.3 | 23.3 | 23.3 | 23.3 | 23.3 | 23.3 | 23.3 | 23.3 | 23.3 | 23.3 |
| C-28 | 28.6 | 28.6 | 28.4 | 28.5 | 28.5 | 28.5 | 28.5 | 29.5 | 29.5 | 29.5 | 29.5 | 29.5 |
| C-29 | 28.3 | 28.3 | 28.3 | 28.3 | 28.3 | 28.3 | 28.3 | 29.4 | 28.6 | 28.6 | 28.6 | 28.6 |
| C-30 | 176.9 | 176.5 | 176.2 | 176.2 | 176.2 | 176.2 | 176.2 | 173.9 | 174.6 | 174.7 | 174.7 | 174.6 |
| OCH₃ | 51.8 | 51.8 | | | | | | | | | | |
| OCH₂CH₃ | | | 60.2 | | | | | 60.3 | | | | |
| OCH₂CH₃ | | | 14.2 | | | | | 14.2 | | | | |
| OCH₂CH₂CH₃ | | | | | | | | | | | | |
| OCH₂CH₂CH₃ | | | | | | | | | | | | |
| OCH₂CH₂CH₃ | | | | | | | | | | | | |
| OCH(CH₃)₂ | 50.6 | | | 41.2 | | | | | 50.6 | | | |
| OCH(CH₃)(CH₃) | 21.8 | | | 21.8 | | | | | 21.8 | | | |
| OCH(CH₃)(CH₃) | 21.8 | | | 21.8 | | | | | 21.8 | | | |
| OCH₂ | | | | | 66.2 | 66.2 | 66.3 | 66.2 | 66.2 | | | |
| 1' | | | | | 136.1 | 136.1 | 136.1 | 136.1 | 136.1 | | | |
| 2' | | | | | 128.3 | 128.3 | 128.3 | 128.3 | 128.3 | | | |
| 3' | | | | | 128.6 | 128.6 | 128.6 | 128.6 | 128.6 | | | |
| 4' | | | | | 128.5 | 128.5 | 128.4 | 128.4 | 128.4 | | | |
| 5' | | | | | 128.6 | 128.6 | 128.6 | 128.6 | 128.6 | | | |
| 6' | | | | | 128.3 | 128.3 | 128.3 | 128.3 | 128.3 | | | |
| NH—CH₂CH₃ | | | | | | 34.3 | | | | | 44.9 | |
| NH—CH₂CH₃ | | | | | | 14.7 | | | | | 14.8 | |
| NH—CH₂CH₂CH₃ | | | | | | | 41.3 | | | | | 42.1 |
| NH—CH₂CH₂CH₃ | | | | | | | 22.8 | | | | | 31.3 |
| NH—CH₂CH₂CH₃ | | | | | | | 11.4 | | | | | 11.4 |
| NH—CH(CH₃)₂ | | 50.9 | | | | | 51.0 | 50.8 | 50.6 | 51.0 | 50.9 | 50.9 |
| NH—CH(CH₃)₂ | | | | | | | | | | | | 50.9 |
| NH—CH(CH₃)(CH₃) | | 22.7 | | | | | 22.7 | 22.8 | 22.8 | 22.8 | 22.8 | 22.7 |
| NH—CH(CH₃)(CH₃) | | 22.7 | | | | | 22.7 | 23.0 | 23.0 | 22.9 | 22.9 | 22.7 |
| NH—CH(CH₃)(CH₃) | | | | | | | | | | | | 22.8 |
| NH—CH(CH₃)(CH₃) | | | | | | | | | | | | 22.9 |

With such synthesis method above, the derivatives of 18β-glycyrrhetinic acid of the present invention including 10, 11, 13-17 and 21-25 can be industrialized manufactured in an easy and convenient platform, and thus put to use in developing medication for cancer suppression, with the derivatives of 18β-glycyrrhetinic acid of the present invention inducing the generation of ROS, activating tumor suppressor gene p53 in cancer cells, and finally resulting in apoptosis of cancer cells. Furthermore, the derivatives of 18β-glycyrrhetinic acid can be given to a target life-form individually or combined with at least one pharmaceutically acceptable medication or composition, cisplatin for example, for modulating tumor cells with minor side effects.

For the sake of proving therapeutic effects of the derivatives of 18β-glycyrrhetinic acid of the present invention, including 10, 11, 13-17 and 21-25, in treating of cancer, human bladder cancer cell line NTUB1, human prostate cancer cell line PC3 cataloged as CRL-1435 (reference to J. Formosan Med. Assoc. 1992; 91:608-13), and immortalized normal human urothelial cells SV-HUC1 cataloged as CRL-9520 are purchased from American Type Culture Collection (ATCC; Rockville, USA) and maintained in a culturing medium respectively till at a preferable density to carry out a serial of trials (comprising trial A to G) for evaluating cytotoxicities of the derivatives of 18β-glycyrrhetinic acid against cancer cells, and mechanisms thereof.

In the present invention, the NTUB1 and the PC3 is but not limit to be maintained in RPMI 1640 medium supplemented 10% fetal bovine serum (FBS), 100 unit/mL penicillin-G, 100 μg/mL streptomycin, and 2 mM L-glutamine, yet the SV-HUC1 is maintained in F12 medium supplemented with 10% fetal bovine serum (FBS), 100 unit/mL penicillin-G, 100 μg/mL streptomycin, and 2 mM L-glutamine, culturing at 37° C. in a humidified atmosphere containing 5% $CO_2$ till at a density of 70% per well, followed by repeatedly suspending cells in each well with an ethylene diamine tetra-acetic acid buffer (EDTA buffer; Merck) and counting cell numbers.

In trial (A), the NTUB1 at a density of $4 \times 10^5$ cells/ml are and assigned to various groups, including groups of (A0+) being a positive control and co-incubated with cisplatin, (A0−) being a negative control, and (A1) to (A27) being co-incubated with compound 1 to 27 as shown in FIGS. 1 to 3 individually at 37° C., in a humidified atmosphere containing 5% $CO_2$ to demonstrate the cytotoxic effect of each compound by evaluating $IC_{50}$ values of each group in a median-effect analysis. In the present invention, the $IC_{50}$ values of each group are presented as mean±standard deviation (SD).

TABLE 2

IC$_{50}$ Values of Each Group in Trial (A) (μM)

| Groups | Compound | IC$_{50}$ ± SD | Groups | Compound | IC$_{50}$ ± SD | Groups | Compound | IC$_{50}$ ± SD |
|---|---|---|---|---|---|---|---|---|
| A0+ | cisplatin | 3.27 ± 0.10 | A1 | 1 | 27.31 ± 5.17 | A2 | 2 | 18.57 ± 1.64 |
| A3 | 3 | 56.5 ± 14.35 | A4 | 4 | 20.23 ± 5.10 | A5 | 5 | 73.54 ± 35.12 |
| A6 | 6 | 24.28 ± 3.98 | A7 | 7 | 57.61 ± 8.80 | A8 | 8 | 20.72 ± 4.97 |
| A9 | 9 | 2.34 ± 0.28 | A10 | 10 | 25.30 ± 2.28 | A11 | 11 | 31.35 ± 0.55 |
| A12 | 12 | 9.41 ± 2.72 | A13 | 13 | 27.76 ± 6.48 | A14 | 14 | 18.20 ± 1.58 |
| A15 | 15 | 42.74 ± 11.15 | A16 | 16 | 49.39 ± 11.52 | A17 | 17 | 30.12 ± 2.41 |
| A18 | 18 | 25.66 ± 1.81 | A19 | 19 | 17.47 ± 2.11 | A20 | 20 | 13.12 ± 5.27 |
| A21 | 21 | 19.44 ± 19.20 | A22 | 22 | 29.17 ± 26.61 | A23 | 23 | 12.75 ± 2.10 |
| A24 | 24 | >50 | A25 | 25 | 4.76 ± 1.15 | A26 | 26 | 15.95 ± 5.30 |
| A27 | 27 | 3.31 ± 0.61 | A0− | — | — | | | |

With reference to TABLE 2, it is noted that the derivatives of 18β-glycyrrhetinic acid in the present invention all share great cytotoxic effect against to cancer cell, especially for compounds 9, 12, 21, 23, 25, and 27 which significantly suppress the growth of cancer cells with a lower concentrate. It is indicated that the derivatives of 18β-glycyrrhetinic acid of the present invention perform well in tumor-suppression, particularly for one which has two carboxylic acid groups at residue C-3 and residue C-30 through a carbamoylation.

In trial (B), the cell lines of NTUB1, PC3, and SV-HUC1 are prepared in 96-well plates and co-incubated with the compounds 21, 23 or 25 in various concentrations of 0, 0.3, 1, 3, 5, 10, 30 and 50 μM, to analyze cytotoxic effects against either cancer cell or normal cells via a modified 3-[4,5-dimethylthiazol-2-yl]-2,5-diphenyltetrazolium bromide (MTT, Sigma Chemical Co.) assay. Specifically, the NTUB1, PC3, and SV-HUC1 are plated at a density of 1800 cells/well in 96-well plates respectively, incubated at 37° C. overnight, and then further incubated with various concentration of the compound 12, 23 and 25 respectively at 37° C. for 72 hours. At co-incubation, 50 μL of MTT (2 mg/mL in PB) is added to each well to react for 3 hours, followed by centrifugating the 96-well plates at 1000 g for 10 min to remove supernatant, adding 150 μL DMSO in each well of the 96-well plates, and determining viability rates of the NTUB1, PC3, and SV-HUC1 cells separately by an absorbance spectrometry at 540 nm with a MRX (DYNEXCO) microplate reader.

Figure 4:
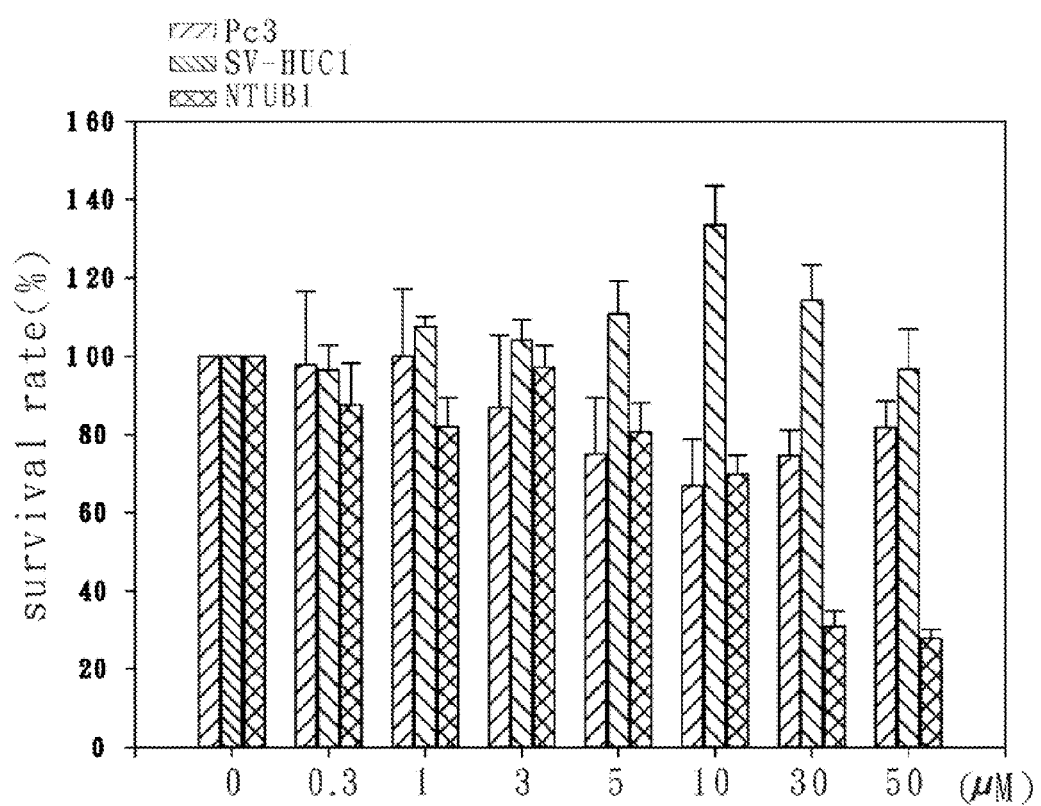
FIG. 4 is a bar chart illustrating survival ratio of three cell lines under a co-cultivation with 21 in the present invention.
Figure 5:
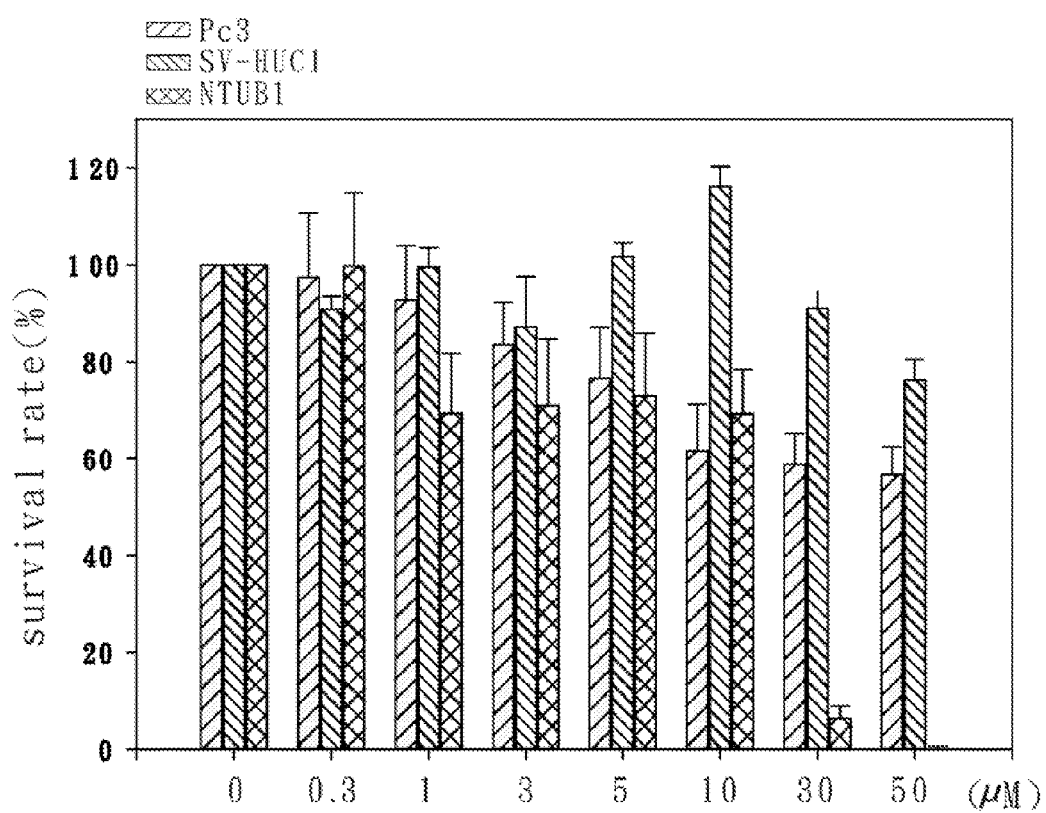
FIG. 5 is a bar chart illustrating survival ratio of three cell lines under a co-cultivation with 23 in the present invention.
Figure 6:
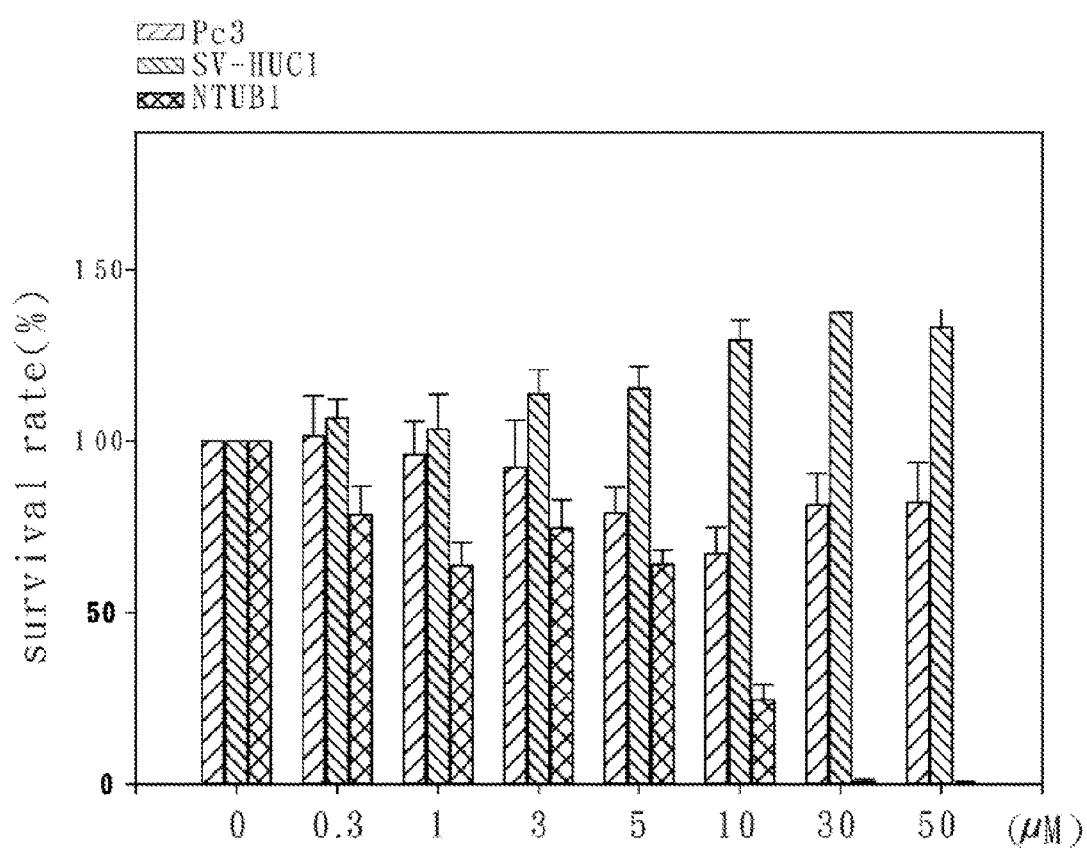
FIG. 6 is a bar chart illustrating survival ratio of three cell lines under co-cultivation with 25 in the present invention.

In FIGS. 4, 5 and 6, it is indicated that compounds of 21, 23 and 25 show cytotoxic effects against to the cancer cells in a dose-dependent manner, particularly in against to NTUB1 cell, but enhance the growth of SV-HUC1 cells. It is suggested that the derivatives of 18β-glycyrrhetinic acid of the present invention will not interfere with the growth of normal cells, but specifically arrest cancer cells, bladder cancer cells and prostate cancer cells for example, and which is capable of being used in pharmaceutical industry, as an active substance of an anti-cancer drug to suppress the progress of cancer cells.

In trial (C), a synergy of the derivatives of 18β-3-glycyrrhetinic acid of the present invention and cisplatin is demonstrated in view of a journal article published by Ping et. al., in 2010 at Urol. Oncol: Semin. Orig. Invest. by maintaining the NTUB1 cells in various condition of medium (with reference to TABLE 3) at 37° C. for 72 hours, and determining cytotoxicities of each medium via MTT assay. In the trial (C), the viability rates of NTUB1 cells reader are also determined by the absorbance spectrometry at 540 nm with a MRX (DYNEXCO) microplate according to trial (B).

TABLE 3

Various Conditions of Medium in Each Groups

| Groups | Medium 12 (μM) | cisplatin (μM) | Groups | Medium 20 (μM) | cisplatin (μM) |
|---|---|---|---|---|---|
| C12-1-1 | 0 | 0 | C20-1-1 | 0 | 0 |
| C12-1-2 | 0 | 5 | C20-1-2 | 0 | 5 |
| C12-1-3 | 0 | 10 | C20-1-3 | 0 | 10 |
| C12-2-1 | 1 | 0 | C20-2-1 | 1 | 0 |
| C12-2-2 | 1 | 5 | C20-2-2 | 1 | 5 |
| C12-2-3 | 1 | 10 | C20-2-3 | 1 | 10 |
| C12-3-1 | 3 | 0 | C20-3-1 | 3 | 0 |
| C12-3-2 | 3 | 5 | C20-3-2 | 3 | 5 |
| C12-3-3 | 3 | 10 | C20-3-3 | 3 | 10 |
| C12-4-1 | 5 | 0 | C20-4-1 | 5 | 0 |
| C12-4-2 | 5 | 5 | C20-4-2 | 5 | 5 |
| C12-4-3 | 5 | 10 | C20-4-3 | 5 | 10 |
| C12-5-1 | 10 | 0 | C20-5-1 | 10 | 0 |
| C12-5-2 | 10 | 5 | C20-5-2 | 10 | 5 |
| C12-5-3 | 10 | 10 | C20-5-3 | 10 | 10 |
| C12-6-1 | 30 | 0 | C20-6-1 | 30 | 0 |
| C12-6-2 | 30 | 5 | C20-6-2 | 30 | 5 |
| C12-6-3 | 30 | 10 | C20-6-3 | 30 | 10 |
| C12-7-1 | 50 | 0 | C20-7-1 | 50 | 0 |
| C12-7-2 | 50 | 5 | C20-7-2 | 50 | 5 |
| C12-7-3 | 50 | 10 | C20-7-3 | 50 | 10 |

Figure 7:
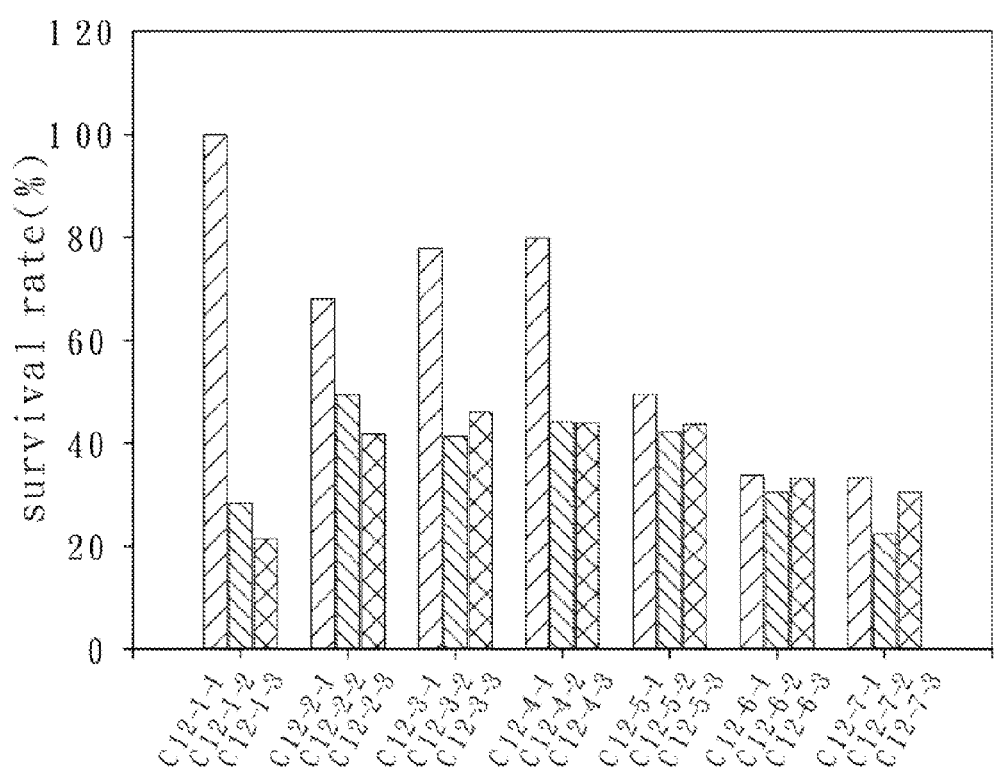
FIG. 7 is a bar chart illustrating survival ratio of three cell lines under a co-cultivation with 12 and cisplatin in the present invention.
Figure 8:
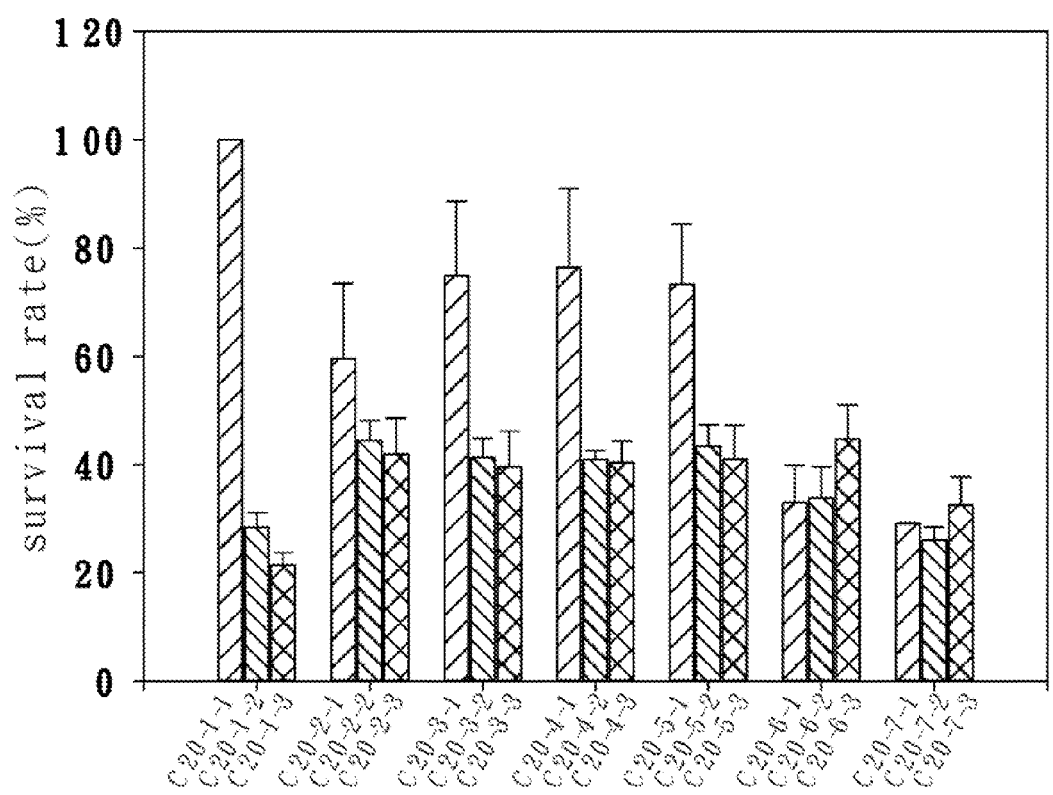
FIG. 8 is a bar chart illustrating survival ratio of three cell lines under a co-cultivation with 20 and cisplatin in the present invention.

In FIGS. 7 and 8, it is indicated that the conventional anti-cancer drug cisplatin, 20, and 12 all has cytotoxic effects against to cancer cells as being applied individually. Furthermore, in cooperation with cisplatin and 12, or cisplatin and 20 also show great performance in cytotoxicity against to cancer cells, preferably for 1 to 5 μM of 12 and 5/10 μM of cisplatin, or for 1 to 5 μM of 20 and 5/10 μM of cisplatin. It is proved that there is a dramatic synergy between the conventional anti-cancer drug, such as cisplatin, and the derivatives of 18β-glycyrrhetinic acid of the present invention, such as 12 and 20. Thus, it is suggested that the derivatives of 18β-glycyrrhetinic acid of the present invention can be given to any target individually or in combination with a conventional anti-cancer drug, in order to effectively suppress cancer cell with a high efficiency but a less dosage of the conventional anti-cancer drug. In this way, the side effects, such as drug-resistance and toxicity, caused by the conventional anti-cancer drug may be reduced and improved when it is in combination with the derivatives of 18β-glycyrrhetinic acid of the present invention.

In trial (D), production of reactive oxygen species (ROS) is analyzed by flow cytometry, since the levels of ROS play an important role in apoptosis. In trial (D), it is supposed to prove that the derivatives of 18β-glycyrrhetinic acid can induce the generation of ROS leading to apoptosis of cancer cells.

Referring to TABLE 4, the NTUB1 cells at a density of 8×10$^5$ cells/ml are prepared and assigned into 5 groups, including D1 to D5, to incubate in various medium for 24 hours. Next, 10 μM of 2,7-dichlorodihydrofluorescein diacetate (H$_2$DCFHDA; Molecular Probes, Eugene, Oreg.) is added to the NTUB1 cells of each group 30 minutes prior than harvest, followed by collecting the NTUB1 cells of each group respectively and washing with PBS buffer. With such arrangement, the 2,7-dichlorodihydrofluorescein diacetate will penetrate into cells, interact with esterase, and degrade to 2,7-dichlorofluorescein (DCF) having green fluorescein, which can be determined by flow cytometer. In trial (D), green fluorescence of intracellular DCF in each group are analyzed immediately by FACScan flow cytometer (Becton Dickinson) at a wavelength of 525 nm.

TABLE 4

Groups Assignment in Trial (D)

| Groups | Medium | ROS (%) |
|---|---|---|
| D1 | — | 47.4 |
| D2 | 20 μM Cisplatin | 63.1 |
| D3 | 1 mM NAC | 26.1 |
| D4 | 10 μM 25 | 66.1 |
| D5 | 25 μM 25 | 85.6 |

In TABLE 4, it is shown that a higher production of ROS is observed in the groups D4 and D5 in comparison with other groups. Therefore, it is believed that the derivatives of 18β-glycyrrhetinic acids of the present invention truly have ability of inducing the generation of ROS in cancer cells.

In order to determine a relationship between the derivatives of 18β-glycyrrhetinic acid of the present invention and cell cycle arrest, trial (E) is carried out by analyzing cell cycle progression by flow cytometry. In trial (E), the NTUB1 cells at a density of 8×10$^5$ cells/ml are prepared and assigned into 7 groups, including E1 to E7, to incubate in various medium, such as 20 μM cisplatin, 25, 50 and 75 μM 25, 1 mM NAC and 50 μM H$_2$O$_2$, for 24 hours, followed by collecting the NTUB1 cells of each group respectively, washing with PBS buffer, fixing in ice-cold methanol at −20° C. for 24 hours, and washing again with PBS buffer. After that, cell cycle progression of each group is determined respectively by incubating with 50 μg/mL propidium iodide (Sigma, Co) and 50 μg/mL RNase A (Sigma, Co) in PBS at room temperature for 30 min, and analyzing by FACScan flow cytometer and Cell Quest sofeware.

TABLE 5

Groups Assignment in Trial (E)

| Groups | Medium | Sub-G1 | G1 | S | G2/M |
|---|---|---|---|---|---|
| E1 | — | 6.68 | 50.64 | 20.37 | 21.08 |
| E2 | 20 μM Cisplatin | 10.35 | 60.91 | 22.09 | 6.65 |
| E3 | 25 μM 25 | 20.39 | 49.51 | 12.69 | 12.68 |
| E4 | 50 μM 25 | 55.71 | 35.72 | 3.15 | 5.22 |
| E5 | 75 μM 25 | 78.39 | 14.69 | 2.79 | 4.00 |
| E6 | 1 mM NAC | 2.66 | 44.41 | 29.18 | 20.18 |
| E7 | 50 μM H$_2$O$_2$ | 9.48 | 27.15 | 23.84 | 20.18 |

In TABLE 5, it is noticed that a treatment of 25, 50 and 75 μM of 25 does not induce cell cycle arrest but induce the population of sub-G1 phase to cancer cells in dose-dependent manner. Furthermore; exposure of cancer cells to 25 leads to not only an increase of sub-G1 phase cells, but also a decrease of S phase cells which mean apoptosis has occurred. Therefore, it is believed that the derivatives of 18β-glycyrrhetinic acid of the present invention, 25 for example, induced cancer cells deaths are mainly due to apoptosis.

In trial (F), mitochondrial membrane potential (MMP) in NTUB1 cells is measured according to a journal article published by Martin et al., at 2009 in PloS one, in which a dysfunction of the mitochondria caused by ROS induced MPP decrease is supposed.

Referring to TABLE 6, the NTUB1 cells at a density of 3×10$^5$ cells/ml are prepared and assigned into 5 groups, including F1 to F5, to incubate in 10 μM carbonyl cyanide 3-chlorophenylhydrazone (CCCP), and 10, 25 and 50 μM of 25 respectively, for 30 minutes, followed by adding 1 μM of 5,5',6,6'-tetrachloro-1,1',3,3'-tetraethylbenzimidaolylcarbocyanine iodide (JC-1) (Molecular Probes, Eugene, Oreg., USA) in each group. Then, the NTUB1 cells in each group are washed with PBS buffer for 3 times, collected in PBS/2% BSA, washed twice by centrifugating at 800 g, 5 minutes and resuspending in 0.3 mL PBS/2% BSA, and finally analyzed by a FACSCalibur flow cytometer (Becton Dickinson), with the FACSCalibur flow cytometer determining and calculating a ratio of JC-1 aggregates (red fluorescence) to JC-1 monomers (green fluorescence) based on levels of MMP in each group.

TABLE 6

Groups Assignment in Trial (F)

| Groups | Medium | R1 (%) | R2 (%) |
|---|---|---|---|
| F1 | — | 95.32 | 4.48 |
| F2 | CCCP | 52.06 | 48.42 |
| F3 | 10 μM 25 | 94.14 | 5.45 |
| F4 | 25 μM 25 | 87.17 | 12.65 |
| F5 | 50 μM 25 | 55.65 | 44.07 |

In TABLE 6, it is pointed out that a treatment of 25, 50 and 75 μM of 25 decrease MPP in cancer cells in a dose-dependent manner, so that the derivatives of 18β-glycyrrhetinic acid of the present invention, 25 for example, truly can suppress cancer cell through decreasing MPP levels in cancer cells.

According to trials (D) to (F), it has been suggested that the derivatives of 18β-glycyrrhetinic acid of the present invention can induce the production of ROS, with overproduction of ROS decrease the mitochondrial membrane potential (MMP), and leading to apoptosis of cancer cells.

In trial (G), expression of p53 is monitored via Western blot analysis in accordance with a journal article published by Son et al., at 2010 in Toxicol. Appl. Pharmacol., in which overproduction ROS induced p53 suppression is observed.

Referring to TABLE 7, the NTUB1 cells at a density of 8×10$^5$ cells/ml are prepared and assigned into 9 groups, including G1-1 to G1-5 and G2-1 to G2-4, to incubate in various medium for 24 hours, followed by harvesting in trypsinization, resuspending in PBS till at a suitable density and collecting the NTUB1 cells of each group respectively.

Next, the NTUB1 cells of each group are further diluted with equal volume of 2× sample buffer, boiled for 10 minutes twice to denature protein therein, and analyzed by SDS-PAGE. After that, proteins on SDS-PAGE datum are transferred to nitrocellulose membranes (Millipore, Billerica, Mass., USA) using a semi-dry blotter, followed by blocking with 5% (w/v) skimmed milk in TBST buffer (100 mM Tris-HCl (pH 7.5), 150 mM NaCl and 0.1% Tween-20), incubating with specific antibodies [including antibodies specific for b-acctin (NB600-501), p-p53 (Ser15) (9284) and p53 (DO1)]. at 4° C. overnight, washing with TBST buffer again and incubated with secondary antibody at room temperature. Finally, western data of each group are visualized on Fuji SuperRX film.

In the present trial, antibody specific to b-acctin (NB600-501) is purchased from Novus Biologicals (Littleton, Colo., USA), antibody specific to p-p53 (Ser 15) (9284) polyclonal antibody is purchased from Cell Signaling (Beverly, Mass., USA) and a monoclonal antibody specific to p53 (D01) is purchased from Santa Cruz Biotechnology (Santa Cruz, Calif., USA).

TABLE 7

Groups Assignment in Trial (G)

| Groups | medium |
|---|---|
| G1-1 | — |
| G1-2 | 10 μM Cisplatin |
| G1-3 | 10 μM 25 |
| G1-4 | 25 μM 25 |
| G1-5 | 50 μM 25 |
| G2-1 | — |
| G2-2 | 50 μM 25 |
| G2-3 | NAC |
| G2-4 | 50 μM 25 + NAC |

Figure 9:
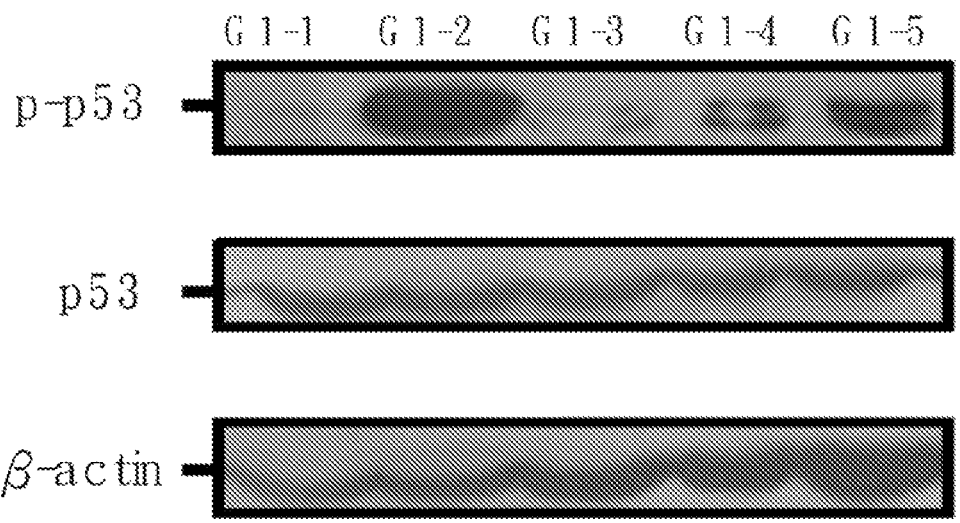
FIG. 9 is a western blot datum illustrating groups G1-1 to G1-5 of 25.
Figure 10:
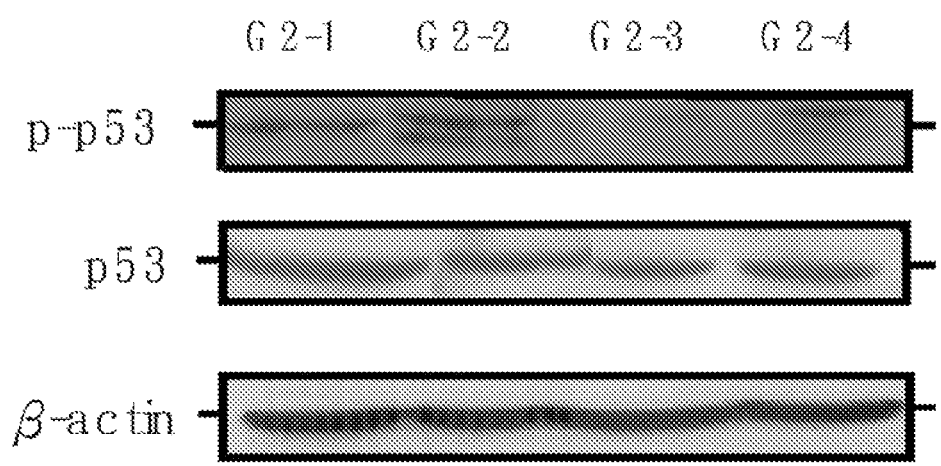
FIG. 10 is a western blot datum illustrating groups G2-1 to G2-4 of 25.

In FIGS. 9 and 10, it is noted that a treatment of 25 increase levels of p-p53 in a dose-dependent manner. Further, a treatment of NAC prevents p53 phosphorylation that stimulated by 25. These data strongly suggested that the generation of ROS played an important role in p53 activation. Also, the derivatives of 18β-glycyrrhetinic acid of the present invention, 25 for example, do induce the activation of p53 and lead to apoptosis of cancer cells.

With the trials of the present invention, we investigate the effect of the derivatives of 18β-glycyrrhetinic acid of the present invention, such as 25, in inducing levels of p53 phosphorylation and ROS, so as to decrease the mitochondrial membrane potential in tumor cells and to result in apoptosis.

Through the present invention, the derivatives of 18β-glycyrrhetinic acid of the present invention, having therapeutic effects in suppressing cancer cells via increasing the levels ROS and the tumor suppressor gene p53 in cancer cells, are provided. Therefore, the derivatives of 18β-glycyrrhetinic acid of the present invention is capable of being use in pharmaceutical industry as an active substance of medication for suppressing cancer cells. The medication of the present invention can be manufactured into any form of medications including a pastil, capsule, powder, pill, and liquid for easy to apply on any life-forms. In general, the medication of the present invention can be given individually or combined with any pharmaceutical acceptable carrier, to effectively suppress cancer cells, particularly for bladder cancer cells or prostate cancer cells.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A derivative of 18β-glycyrrhetinic acid being selected from a group consisting of structure I and structure II:

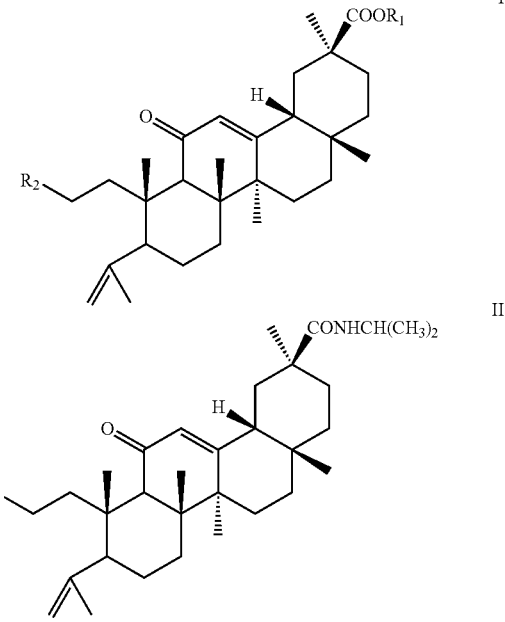

wherein residue $R_1$ is $CH_3$ and residue $R_2$ is $COOCH(CH_3)_2$ or $CONHCH_2(CH_3)_2$, or residue $R_1$ is $CH_2C_6H_5$ and residue $R_2$ is $COOCH_2CH_3$, $COOCH(CH_3)_2$, $CONHCH_2CH_3$, $CONHCH_2CH_2CH_3$ or $CONHCH_2(CH_3)_2$;

wherein residue $R_3$ is selected from one of $COOCH_2CH_3$, $COOCH(CH_3)_2$, $CONHCH_2CH_3$, $CONHCH_2CH_2CH_3$ and $CONHCH_2(CH_3)_2$.

2. A method for treating bladder cancer, by administrating an effective amount of a derivative of 18β-glycyrrhetinic acid to a subject in need thereof to treat bladder cancer cells wherein the derivative of 18β-glycyrrhetinic acid, being selected from a group consisting of structure I and structure II:

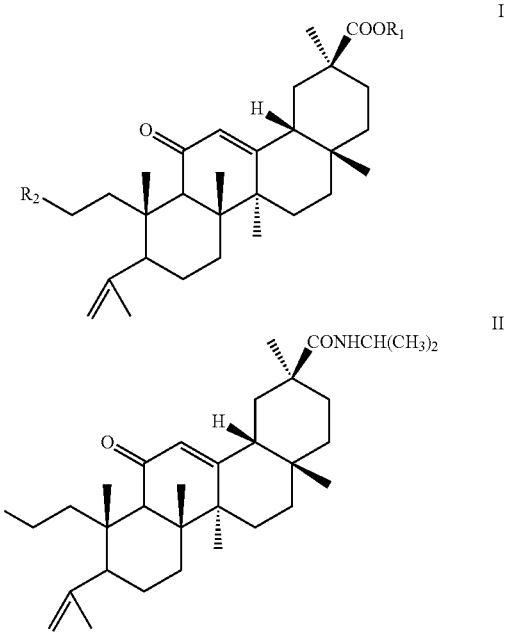

wherein residue $R_1$ is $CH_3$ and residue $R_2$ is $COOCH(CH_3)_2$ or $CONHCH_2(CH_3)_2$, or residue $R_1$ is $CH_2C_6H_5$ and residue $R_2$ is $COOCH_2CH_3$, $COOCH(CH_3)_2$, $CONHCH_2CH_3$, $CONHCH_2CH_2CH_3$ or $CONHCH_2(CH_3)_2$;

wherein residue $R_3$ is selected from one of $COOCH_2CH_3$, $COOCH(CH_3)_2$, $CONHCH_2CH_3$, $CONHCH_2CH_2CH_3$ and $CONHCH_2(CH_3)_2$.

* * * * *